United States Patent
Petrucelli et al.

(10) Patent No.: US 6,292,690 B1
(45) Date of Patent: Sep. 18, 2001

(54) APPARATUS AND METHOD FOR MEASURING BIOELECTRIC IMPEDANCE

(75) Inventors: Steven P. Petrucelli, Cranbury; Stephen A. Orbine, Bernardsville, both of NJ (US)

(73) Assignee: Measurement Specialities Inc., Fairfield, NJ (US)

( * ) Notice: Subject to any disclaimer, the term of this patent is extended or adjusted under 35 U.S.C. 154(b) by 0 days.

(21) Appl. No.: 09/481,584

(22) Filed: Jan. 12, 2000

(51) Int. Cl.$^7$ ................................................ A61B 5/05
(52) U.S. Cl. ................................................ 600/547
(58) Field of Search .................... 600/547, 546, 600/506; 177/4, 245; 33/511, 512, 515; 324/98, 99 R, 100, 99 D, 101

(56) References Cited

U.S. PATENT DOCUMENTS

| | | |
|---|---|---|
| 4,144,763 | 3/1979 | Vogelman . |
| 4,578,635 * | 3/1986 | Mee et al. ............... 324/62 |
| 4,831,527 | 5/1989 | Clark . |
| 4,947,862 * | 8/1990 | Kelly .................... 128/734 |
| 5,052,405 | 10/1991 | Batchelder . |
| 5,105,825 | 4/1992 | Dempster . |
| 5,335,667 | 8/1994 | Cha et al. . |
| 5,372,141 | 12/1994 | Gallup et al. . |
| 5,415,176 * | 5/1995 | Sato et al. .............. 128/734 |
| 5,435,315 | 7/1995 | McPhee et al. . |
| 5,449,000 * | 9/1995 | Libke et al. ............. 128/734 |
| 5,579,782 | 12/1996 | Masuo . |
| 5,595,189 | 1/1997 | Naim et al. . |
| 5,611,351 * | 3/1997 | Sato et al. .............. 128/734 |

OTHER PUBLICATIONS

Rudolph J. Liedtke, *The Fundamentals of Bioelectrical Impedance, Analysis,* Feb. 1, 1998 (10 pages).

Rudolph J. Liedtke, *Bioelectrical Impedance Primciples,* Apr. 1, 1997, (12 pages).

Bia Testing Procedure, Feb. 24, 1998, (2 pages).

Testing Your Bia System, Feb. 24, 1998 (2 pages).

* cited by examiner

*Primary Examiner*—Marvin M. Lateef
*Assistant Examiner*—Eleni Mantis Mercader
(74) *Attorney, Agent, or Firm*—Arthur L. Plevy; Duane Morris & Heckscher (57) ABSTRACT

A circuit for measuring body impedance comprising a voltage source having a predetermined frequency and a current source; a first pair of electrodes adapted to receive one portion of the body for applying said current source to said body; a second pair of electrodes adapted to receive another portion of the body for sensing a voltage therebetween; a comparator having first and second inputs and an output for producing an output signal based on signals applied to said first and second inputs; an instrumentation amplifier arrangement coupled to one of said comparator inputs and responsive to the voltage across the second pair of electrodes for providing an input signal to said first comparator input; a variable resistor coupled to the second input of said comparator and responsive to said voltage source for developing a first voltage signal applied to said second comparator input; and a processor responsive to the output signal of the comparator for controlling the resistance of the variable resistor to cause a corresponding change in said first voltage, whereby when said voltage at said first input corresponds to the voltage at said second input of said comparator; said comparator output signal transitions from a first state to a second state to cause the processor to terminate resistor adjustment, whereby the body impedance value corresponds to the resistance value of the variable resistor.

25 Claims, 11 Drawing Sheets

APPARATUS AND METHOD FOR MEASURING BIOELECTRIC IMPEDANCE

FIELD OF INVENTION

The present invention relates to measurement devices in general and more particularly to a method and apparatus for measuring impedance of a biological organism.

DESCRIPTION OF PRIOR ART

There exist in the prior art numerous methods and apparatus for measuring or determining body impedance and body composition (i.e. body fat).

For instance, U.S. Pat. No. 4,144,763 discloses a method of measuring body fat using Boyle's law. U.S. Pat. No. 4,831,527 discloses a system where a fat-to-lean ratio is measured by having a subject stand on a platform and raise his or her heels and then allowing the weight to fall near a transducer to produce a force. The subject's stomach and other flesh continue to move in a downward direction after skeletal motion has stopped, resulting in a downward force which is registered as a data peak and measured by a computer. A technique for measuring body fat by immersing the subject in a liquid is disclosed in U.S. Pat. No. 5,052,405. U.S. Pat. No. 5,105,825 teaches a method of measuring body fat by transferring controlled volumes of gas between two chambers and measuring pressure while U.S. Pat. No. 5,335,667 measures body composition using bioelectric impedance measurements.

In U.S. Pat. No. 5,372,141 a body fat calculator is described which basically measures body fat by the impedance of the network and uses various algorithms after measuring the impedance of the body.

A physical fitness evaluation system is disclosed in U.S. Pat. No. 5,435,315 which, besides measuring body fat, can calculate the overall fitness of the individual. This means for measuring body fat uses a large caliper in conjunction with a variable resistor. Pat. No. 5,579,782 shows a high frequency signal generator which is used to measure impedance. The body fat ratio is calculated from those measurements.

U.S. Pat. No. 5,595,189 relies on measuring body fat by determining a subject's weight using two gases at different densities. The weight of the person is measured with a precision balance and the person's body fat is determined by the density of both of the gaseous environments.

U.S. Pat. No. 5,415,176 issued on May 16, 1999 entitled APPARATUS FOR MEASURING BODY FAT, to Sato et al. discloses a method of determining body impedance using two pairs of electrodes placed at the toes and heels of a person, applying a constant current to the toe electrodes, measuring the voltage at the heel electrodes, and calculating the impedance as the ratio of the measured voltage over the constant current. The body fat is then calculated from the body impedance. U.S. Pat. No. 5,611,351 issued on Mar. 18, 1997 entitled METHOD AND APPARATUS FOR MEASURING BODY FAT, to Sato et al. is a continuation of U.S. Pat. No. 5,415,176 and calculates body fat from the impedance value and the person's height and weight.

However, numerous problems and limitations are encountered with the application of each of the above systems and methods for determining body impedance (or body fat). Such limitations include accuracy and reliability, portability and ease of use, size and circuit complexity, and response time. Accordingly, a method and apparatus for determining body impedance which obviates these shortcomings is highly desired.

SUMMARY OF THE INVENTION

A circuit for measuring body impedance comprising a voltage source having a predetermined frequency and a current source; a first pair of electrodes adapted to receive one portion of the body for applying the current source to the body; a second pair of electrodes adapted to receive another portion of the body for sensing a voltage therebetween; a comparator having first and second inputs and an output for producing an output signal based on signals applied to the first and second inputs; a differential amplifier arrangement coupled to one of the comparator inputs and responsive to the voltage across the second pair of electrodes for providing an input signal to the first comparator input; a variable resistor coupled to the second input of the comparator and responsive to the voltage source for developing a first voltage signal applied to the second comparator input; and a processor responsive to the output signal of the comparator for adjusting the resistance of the variable resistor to cause a corresponding change in the first voltage, whereby when the voltage at the first input corresponds to the voltage at said second input of said comparator, the comparator output signal transitions from a first state to a second state to cause the processor to terminate resistor adjustment, whereby the body impedance value corresponds to the adjusted resistance value of the variable resistor.

An apparatus for measuring body composition in a patient's body comprising a measuring station for measuring impedance between the patient's feet and an operating circuit coupled to the measuring station, the measuring station including a base on which a patient can stand, first and second pairs of electrodes mounted on the base, the first pair of electrodes adapted to receive one portion of the body for transmitting a drive current thereto; the second pair of electrodes adapted to receive another portion of the body for sensing a voltage therebetween; a comparator having inputs for receiving first and second input signals and an output terminal for providing an output signal; an amplifier arrangement responsive to the voltage across the second pair of electrodes for providing one input signal to the comparator; a digital potentiometer coupled between the first pair of electrodes and the second input of the comparator for providing a second input signal thereto; and a processor responsive to the output signal of the comparator for producing a control signal to the potentiometer for adjusting the resistance of the potentiometer to cause a corresponding change in voltage of the second input signal; whereby when the voltage of the second input signal corresponds to the voltage output produced by the amplifier arrangement, the comparator output signal transitions from a first state to a second state indicative of a null condition, whereby the body impedance value corresponds to the resistance of the potentiometer; and an operating circuit coupled to the measuring station for determining body composition as a function of body impedance value.

DETAILED DESCRIPTION OF THE PREFERRED EMBODIMENT

Before embarking on a detailed discussion, the following should be understood. As is well known, the use of body impedance analysis (BIA) to estimate body composition is based on the volume conductor theory. This theory suggests that the volume of a conductor can be determined by its impedance to current flow. The impedance of a conductor is proportional to its length and is inversely proportional to its cross-sectional area. Thus, the impedance Z of a conductor may be characterized by the equation $Z=w*(L/A)$ where w is specific impedance, L is conductor length, and A is cross-sectional area of the conductor. Similarly, the volume V of a conductor can be calculated by measuring the length and the specific impedance of the conductor ($V=w*(L*L/Z)$). Lean Body Mass (LBM), defined as total body mass less fat body mass, may be estimated since it is known that LBM is a function of total body weight. Once LBM is known, the percentage of body fat (% BF) can be determined according to the equation $\% BF=100*(Wt-LBM)/Wt$ where % BF is percent body fat, LBM is lean body mass, and Wt is total body weight.

The present invention provides several advantages over the prior art. First the present invention eliminates the need for handgrips which are often used to determine bio-impedance. Second, the body impedance measurement apparatus and method of the present invention does not require measurement of phase, reactance values, nor require the measurement of multiple frequency signals and voltages to arrive at a body impedance. Still further, conventional devices which drive the body with a known reference current and which use a second pair of electrodes to measure a voltage therebetween require circuitry for demodulating, rectifying, and performing A/D conversion of the measured voltage signal in order to arrive at a body impedance estimate ($Z=V/I$). The present invention eliminates the need for such complex and costly conversion circuitry through the application of a synthesized reference value and matching of an unknown value (Z) to the reference value. The invention thus provides a simple, fast, accurate, and cost-effective way to determine body impedance and hence body fat.

Figure 1A:
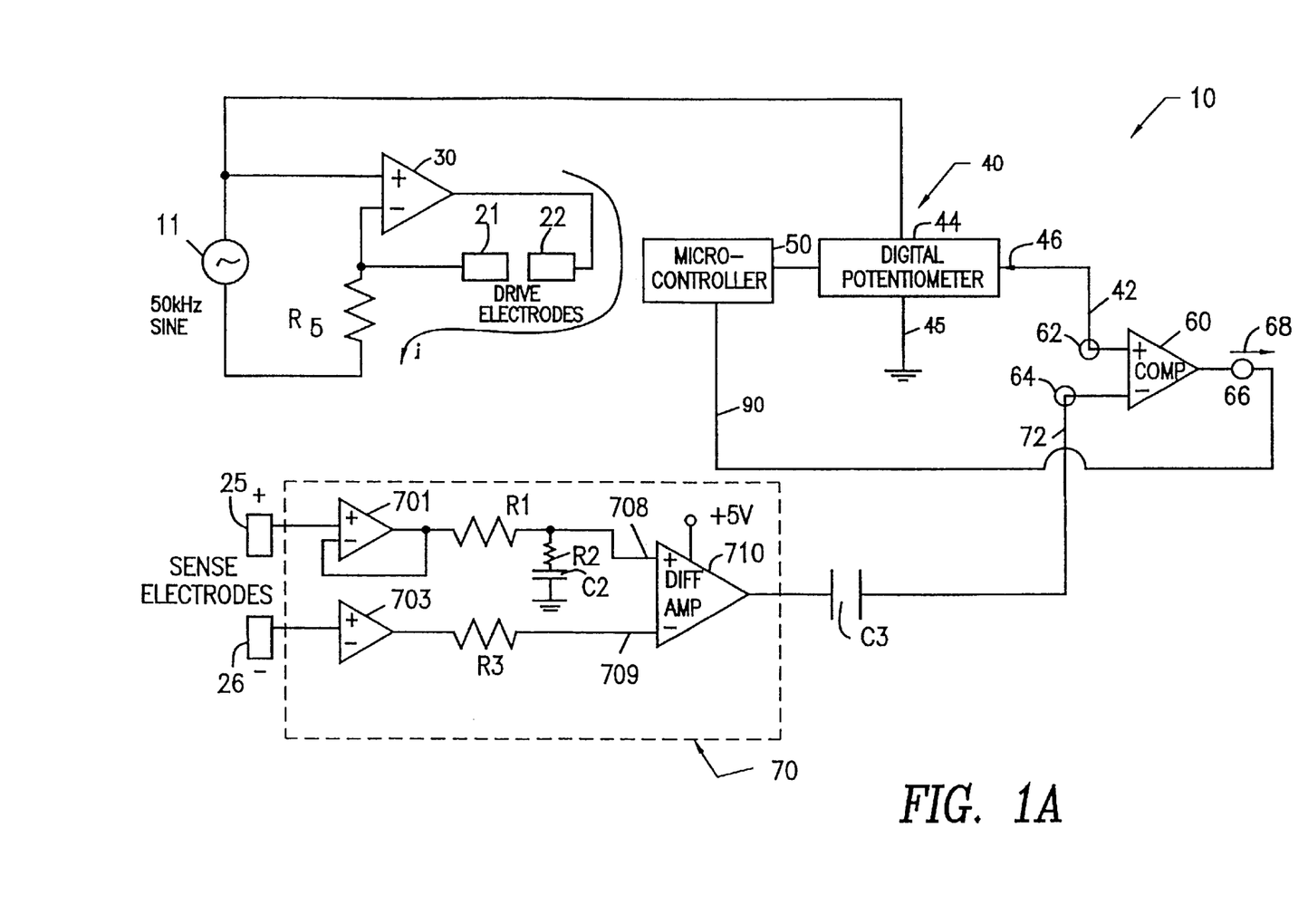
FIG. 1A illustrates a schematic circuit for measuring body resistance or impedance according to an embodiment of the present invention.

Referring now to FIG. 1A, there is depicted a schematic view of an electronic circuit 10 for measuring body resistance or impedance according to the present invention. The circuit comprises a sine wave (steady state) voltage source 11 of about 50 kHz (kilohertz) which is converted to a current drive source of less than 1 mA (milli ampere) at 50 kHz using a conventional voltage to current converter circuit 30. In the preferred embodiment the current is a constant current of approximately 800 uA (micro amperes). The low constant current source applied at this frequency is intended to reduce skin capacitance. Drive electrodes 21,22 interface to a first portion of the body (e.g. are coupled to the toes) and are in the feedback loop of amplifier 30. This same 50 kHz sine wave voltage source is also fed to terminal 44 of digitally controlled potentiometer 40. The potentiometer has terminal 45 coupled to ground or reference potential while the center tap 46 or wiper position for this potentiometer is selected digitally via microcontroller 50. The tap of the potentiometer is n times the voltage of the 50 kHz oscillator 11 (0<n<1) and is applied to the input terminal 62 of comparator 60. In a preferred embodiment, the digital potentiometer is stepped in increments of 10 ohms so as to range between 0 and 1000 ohms (1K). Thus, step n ranges from 0 to 100 steps in 10 ohm increments.

Figure 1B:
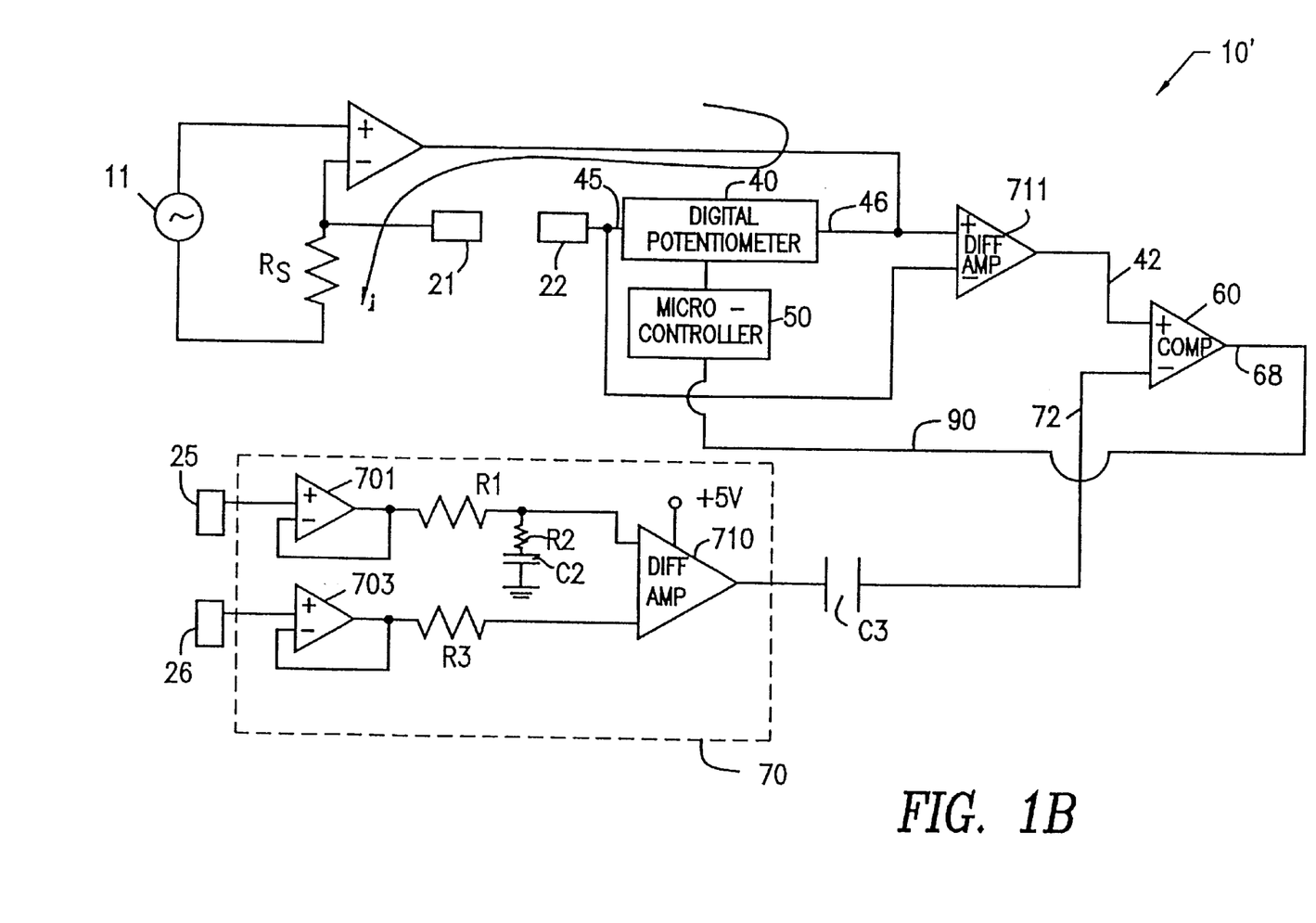
FIG. 1B illustrates a schematic circuit for measuring body resistance or impedance according to an alternative embodiment of the present invention.
Figure 1C:
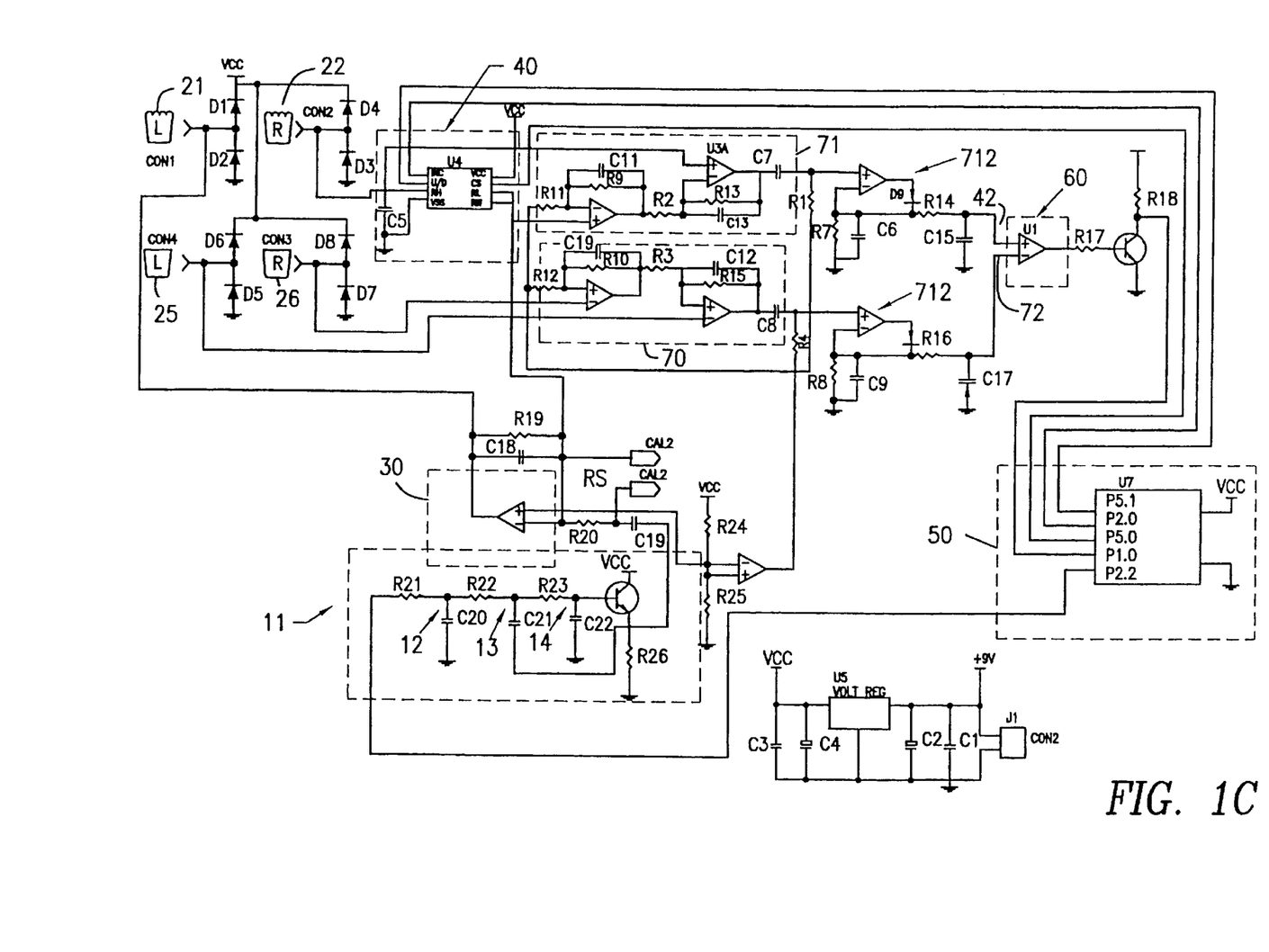
FIG. 1C is a more detailed schematic circuit for measuring body resistance or impedance as shown in FIG. 1B.
Figure 1D:
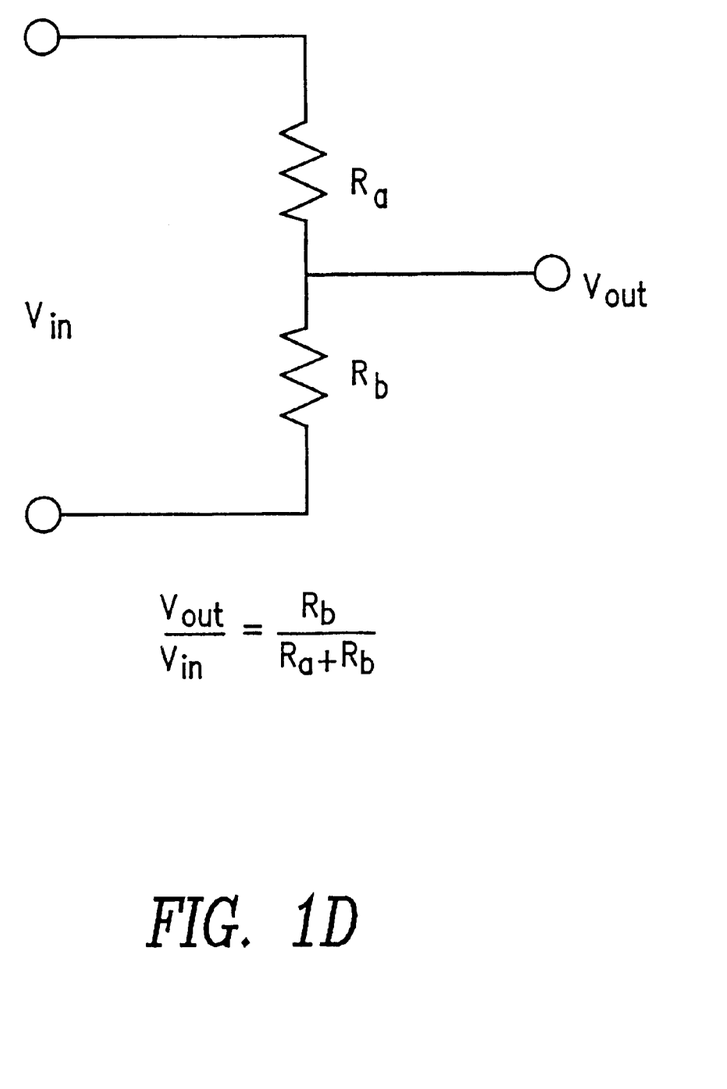
FIG. 1D is a circuit schematic representation of a typical voltage divider construct of a potentiometer.

FIG. 1D shows a circuit schematic representation of a typical voltage divider construct of the potentiometer wherein:

$Ra+Rb=Rtotal=Fixed=1000$ ohms (1kohm);

$[Rb/(Ra+Rb)]*Vi=Vout$ $n*100=Rb$.

The second pair of electrodes 25, 26 are used as voltage sense electrodes where no current flows. The electrodes interface to a second portion of the body (e.g. are coupled to the heels). The potential across these electrodes is applied as input to a standard 3 op-amp instrumentation amplifier (differential amplifier) arrangement 70. The amplifier arrangement 70 comprises first and second buffer amplifiers 701 and 703, each buffer having its non-inverting input terminal coupled to electrodes 25 and 26, respectively. The outputs of each of buffer amplifiers 701 and 703 pass through respective resistors R1 and R3 and are fed into terminals 708 (non-inverting input) and 709 (inverting input) of differential amplifier 710. Resistor R2 and capacitor C2 are serially coupled between node 705 (non-inverting input) and ground potential and operate to filter noise components and to protect the bias point of differential amplifier 710 (V/2). The output signal 72 of the differential amplifier arrangement is applied to terminal 64 of comparator 60 through coupling capacitor C3. Comparator 60 accepts as an input at terminal 62 the voltage signal 42 developed at the center tap of digital potentiometer 40. The comparator compares the microcontroller-selected voltage signal 42 developed at the tap position of digital potentiometer 40 with the voltage signal 72. The comparator outputs a signal 68 at output terminal 66 based on the magnitude of the two input signals 42 and 72.

The comparator output 68 from output terminal 66 indicates whether the center tap of the potentiometer 40 exceeds the voltage signal 72. The comparator output is, in the preferred embodiment, a binary output signal corresponding to either a "high" (binary 1) or "low" (binary 0) state. The output signal 68 is applied via line 90 to microcontroller 50. If signal 42 is greater than signal 72, the output signal 68 from the comparator is "high". In a preferred embodiment, this "high" signal indicates to the microcontroller to provide a control signal to decrease the resistance at the center of digital potentiometer 40 so as to decrease the voltage of signal 42. The digital potentiometer comprises n steps of a predetermined increment (for example 10 ohms). In this manner the resistance of the potentiometer and hence voltage signal 42, is incrementally adjusted in response to the comparator output based on the step count n and the increment value. That is, the microcontroller, in response to output signal 68, sets or adjusts the center tap of the digital potentiometer to a different resistance value each iteration in order to find the point where the output of comparator 60 experiences a state transition. At the point where the voltage signal 42 equals (or is less than) voltage signal 72, the output of the comparator transitions from a "high" to "low" value. When the output of the comparator changes state (from "high" to "low", for example) the comparator is effectively nulled, and the microcontroller in response to detection of a state change terminates further adjustment of the potentiometer resistor value. The bio impedance Z is then determined directly as the number of steps or adjustments n, times the value of the center tap resistance increment (e.g. 10 ohms) of the digital potentiometer 40. This corresponds to the voltage value of the sense electrodes divided by the constant current at the drive electrodes 21, 22.

Note that while the above description is predicated on a "high" to "low" transition of the comparator and decrementing the voltage signal 42 applied at comparator terminal 62 through potentiometer adjustment, it is understood that a "low" to "high" transition detection and incrementing of the voltage signal 42 through adjustment of the potentiometer resistance is of course, also contemplated.

From the above discussion one can see that the microprocessor in combination with the digital potentiometer and comparator operate as a closed-loop servo mechanism to arrive at a bio-impedance based on the drive current and sensed voltage in a very short time. In operation, the aforementioned servo structure advantageously arrives at the body impedance in substantially less time than other techniques (approximately one second), and without the use of additional electronic circuitry, such as analog to digital converters. This is because the impedance is measured directly. The circuit of the present invention thus enables one to measure bio impedance with increased speed and accuracy and with a minimum of circuit components.

An alternative embodiment of the aforementioned impedance measurement circuit for determining bio impedance is illustrated in FIG. 1B. As shown in FIG. 1B, the potentiometer 40 is coupled between differential amplifier arrangement 711 and body electrodes 21, 22 within the feedback loop of the circuit such that the drive current I through the body electrodes 21 and 22 also passes through the potentiometer 40. The circuit components 701, 703, and 710 coupled to voltage sense electrodes 25 and 26 (in electrical contact with the heels of a person) for generating voltage signal 72 for input to the inverting input of comparator 60, have been discussed above with reference to FIG. 1A, and thus will not be detailed further. The pair of electrodes 21 and 22 are in electrical contact with the toes of the left and right feet, respectively and receive the constant 50 kHz drive current I generated by voltage to current converter arrangement 30 acting on sinusoidal voltage signal 11. The voltage signals at terminals 45 and 46 indicative of the voltage drop across potentiometer 40 are applied to differential amplifier 711 so as to produce signal 42 at the non-inverting input of comparator 60. As in FIG. 1A, the output 68 of the comparator represents a binary "high" or "low" signal which is fed back to micro controller 50. In response to the output signal 68, the micro controller provides a digital control signal to potentiometer 40 to adjust the potentiometer resistance a predetermined amount. If signal 42 is greater than signal 72, the output signal 68 from the comparator is "high". In a preferred embodiment, this "high" signal indicates to the microcontroller to provide a control signal to decrease the resistance of digital potentiometer 40 so as to decrease the voltage of signal 42. The digital potentiometer comprises n steps of a predetermined increment (for example 10 ohms). In this manner the resistance of the potentiometer and hence voltage signal 42, is incrementally adjusted in response to the comparator output based on the step count n and the increment value. That is, the microcontroller, in response to output signal 68, sets or adjusts the digital potentiometer to a different resistance value each iteration in order to find the point where the output of comparator 60 experiences a state transition. At the point where the voltage signal 42 equals (or is less than) voltage signal 72, the output of the comparator transitions from a "high" to "low" value. When the output of the comparator changes state (from "high" to "low", for example) the comparator is effectively nulled, and the microcontroller in response to detection of the state change, terminates further adjustment of the potentiometer resistor value. The bio impedance Z is then determined directly as the number of steps or adjustments n, times the value of the tap resistance increment (e.g. 10 ohms) of the digital potentiometer 40.

FIG. 1C is a detailed schematic diagram which includes specific circuit components which perform the actual functions depicted in the high level schematic circuit shown in FIG. 1B. Dashed lines and corresponding reference numerals have been included within the actual circuit implementation of FIG. 1C to better illustrate those parts corresponding to that described within FIG. 1B.

For example, referring now to FIG. 1C, the constant voltage source 11 is formed by a 4 MHz oscillator connected to the microprocessor 50 to develop a square wave voltage signal at approximately 50 KHz (actually 56 KHz) which is acted on by the low-pass filter arrangement 12, 13 14. The low-pass filter arrangement filters the first, third and fifth harmonics of the square wave voltage signal to provide a sinusoidal voltage signal 11 of approximately 50 kHz. The voltage to current converter arrangement 30 includes circuit component designated U2A and having part number JRC2112 as manufactured by Japan Radio Corporation (JRC). Resistor R20, which is an arbitrary schematic designation, has a value of 2000 ohms (2K) and corresponds to set resistor Rs depicted in FIG. 1B. Calibration pads CAL1, CAL2 are illustrated in FIG. 1C to tune and calibrate the circuit. The differential amplifier arrangement 711 comprises amplifiers designated as U3A and U3B coupled to digital potentiometer 40 connected within the feedback loop of current electrodes 21 and 22. The second pair of electrodes 25, 26, are used as voltage sense electrodes where no current flows. The potential across these electrodes is applied as input to instrumentation amplifier arrangement 70 consisting of circuit components designated as U3C and U3D and associated resistor and capacitor network circuitry. The circuit diagram of FIG. 1C also includes rectifier circuitry 712 to provide rectified DC voltage signals to the input terminals of comparator 60.

The micro-controller having exemplary part number designation KS57C2308 as manufactured by Samsung and arbitrary identifier U7 is coupled to digital potentiometer 40 (U4, exemplary part number X9C102) for providing chip select or enable line (CS), step (INC) and direction (U/D) associated with the resistance of the potentiometer. As previously mentioned, in response to the signal at the output of the comparator, the microcontroller provides a control signal to adjust the resistance of the potentiometer by a predetermined amount. This, in turn, causes a corresponding change in the level of voltage signal 42 developed at the input of the comparator. The comparator output is again fed back to the microcontroller which adjusts the resistance value based on the output of the comparator. Thus, the micro controller operates as a servo mechanism by adjusting the resistance of the potentiometer in a stepped amount in response to the comparator output signal to determine body impedance. Note that, while the above servo structure has been described with reference to a potentiometer, it is also contemplated that another electronic device, such as an A/D converter or other device which associates a voltage signal with a resistance value, may also be utilized.

Figure 2:
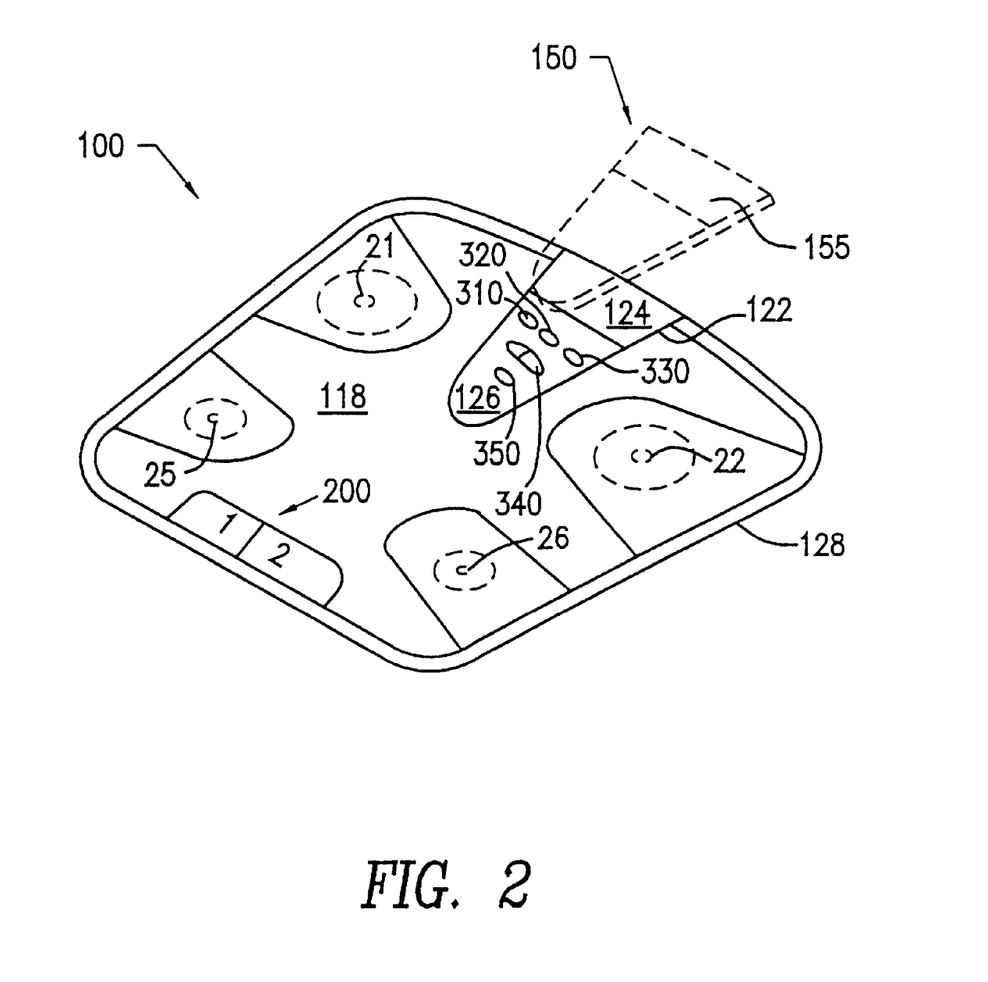
FIG. 2 is a schematic view of a body impedance or body fat measuring device incorporating the body resistance circuitry of FIG. 1 according to an embodiment of the present invention.

The electronic circuit for carrying out the body impedance measurement method may be placed within the housing of an electronic body weighing scale 100 as depicted in FIG. 2. Referring now to FIG. 2, the electronic body weighing scale comprises a platform 118, supports 128 positioned beneath the platform, and a display assembly 122. Each support 128 contains a piezoresistive sensor element or load cell (not shown) that changes an electrical parameter (e.g. resistance) in response to a weight applied to the platform. Conductors (not shown) operate to couple each of the sensors to the display assembly 122. The display assembly is attached to the platform so as to provide a convenient interface for user input and for display purposes.

The display assembly is located at the top front portion of the scale platform and comprises a display portion 124 such as an LCD display, for example, for viewing the results of a measurement. The assembly further includes an interface portion 126 for entering user input data. Interface portion 126 includes push buttons sized sufficient to enable input via a user's toe. In a preferred embodiment, a protective member 150 is hingedly connected to the platform to cover and protect the display area when in the down position, and to provide access to the display area in the up position. The protective member is preferably made of a durable material such as plastic having a transparent portion 155 for viewing the display portion when in the closed or down position.

Referring again to FIG. 2, the platform is formed of an insulating material, and includes a pair of conductive electrodes 25, 26 for a patient's heels and a pair of electrodes 21, 22 for a patient's toes. The electrodes are mounted symmetrically with respect to the width of the platform. This allows the patient to stand upright so that the feet are not touching. In a preferred form of the invention, the electrodes 25, 26 and 21, 22 can be at least partially, if not wholly, formed of a conductive resin, such as a carbon filled resin. Alternatively, a conductive metal coating on a plastic, chroming or a conductive paint can be utilized. The electrodes are set sufficiently far apart from one another so as to eliminate the influence of a potential distribution.

When the patient's heels and toes are contacted by corresponding electrodes 25, 26 and 21, 22, and the scale is activated, the oscillator circuit 11 generates a 50 kHz constant current source at the drive electrodes 21, 22 and the impedance measurement process is initiated. The sensed voltage at the heel electrodes 25, 26 is applied through the instrumentation amplifier arrangement 70 (FIGS. 1A,B,C) and output signal 72 is applied to the input terminal 64 of comparator 60. Note that, while the preferred embodiment has been described wherein the body impedance is determined using electrodes positioned at the heels and toes of a patient, the present invention is not limited to such an application. It is contemplated that the body impedance measurement technique described herein may be utilized by connecting the electrodes to other body portions. For example, body impedance may be measured through a first pair of electrodes disposed within a set of hand grips, for example, for contacting a patient's hands, and a second pair of electrodes in contact with portions of a patient's feet. Similarly, a pair of electrodes coupled to a belt fastened around a patient's waist and a second pair of electrodes coupled to a patient's arms, chest, legs or feet, for example, may also be implemented to determine the body impedance. Numerous other electrode locations and positions for placing the electrodes onto body portions to measure the body impedance are contemplated.

The scale of FIG. 2 further includes a body impedance/body fat activation and user selection switch 200 located at the bottom front portion of the scale platform for activating the body impedance and body fat determination process. Depressing the switch to either the first position (1) or second position (2) activates the body impedance circuitry and causes the microprocessor to retrieve the input characteristics of the particular user associated with the selected switch position.

Figure 3A:
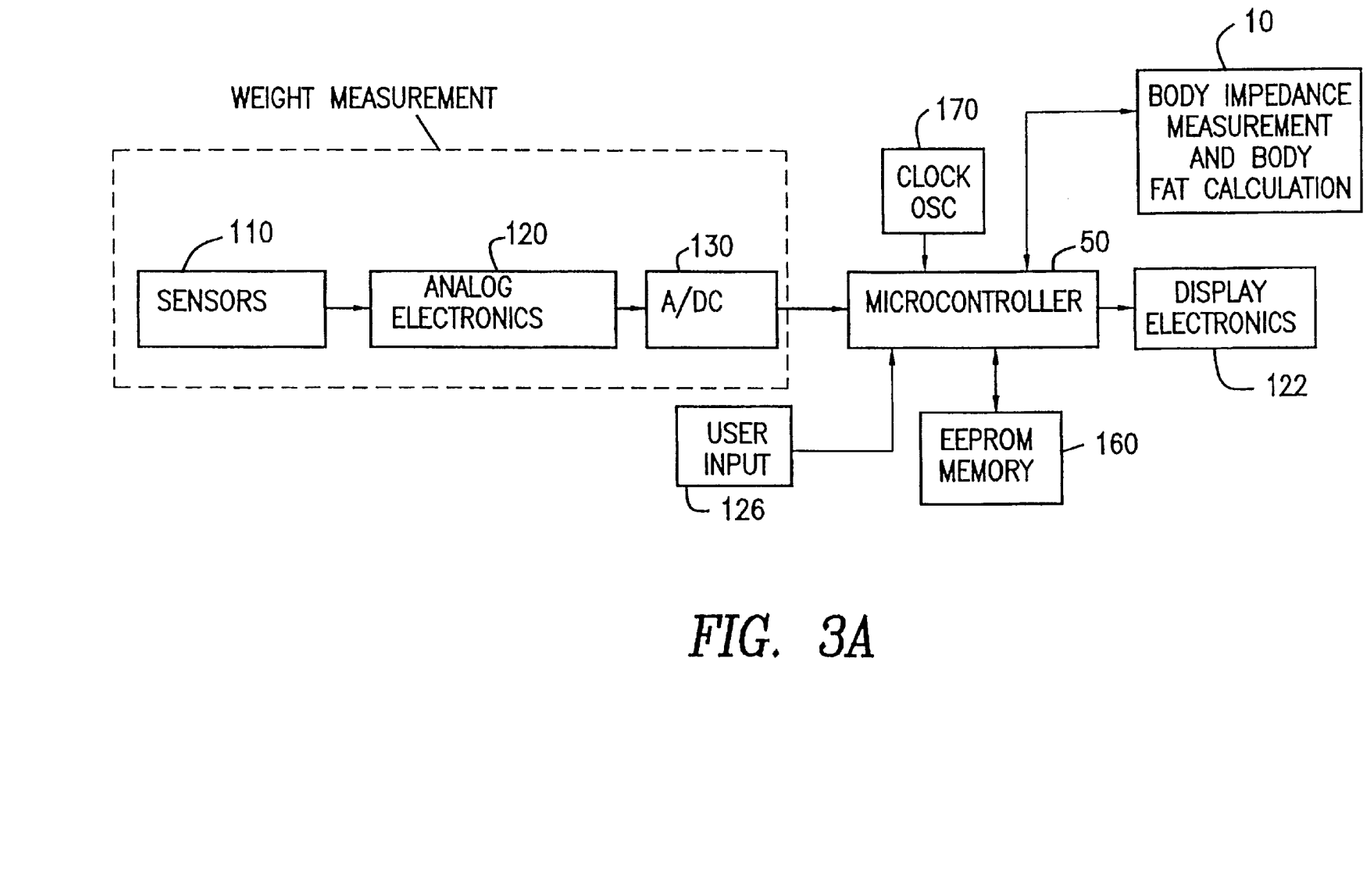
FIG. 3A is a block diagram of the major functional components of the body impedance or body fat measuring device according to an embodiment of the present invention.

As shown in the block diagram of an exemplary electrical circuit for the weight and body fat scale in FIG. 3A, force sensor module 110 comprising each of the piezoresistive sensors within the platform operates to sense the weight of a user for generating a signal indicative of the relative amount of weight sensed. Analog electronics module 120 include calibrating circuits which enable each of the individual sensor elements to provide a response that reflects an accurate proportional share of the total weight applied to the platform and a combining junction for combining each of the individually calibrated piezoresistive sensor signals. The analog electronics circuit is coupled to sensor module 110 via conductors. Analog to digital converter 130 operates to convert the analog calibrated signal into a digital signal representation for input into processor (microcontroller) 50.

Processor 50 comprises a digital microprocessor controller having a clock oscillator 170 operating at approximately 4 MHz to generate a 50 KHz signal, memory 160 and user input interface 126 for accepting data from a user. The digital microprocessor includes software programs or algorithms which operate to calculate body fat based on the determined body weight, the determined body resistance (module 10) and patient data, such as height, age, and gender, for example.

Figure 3B:
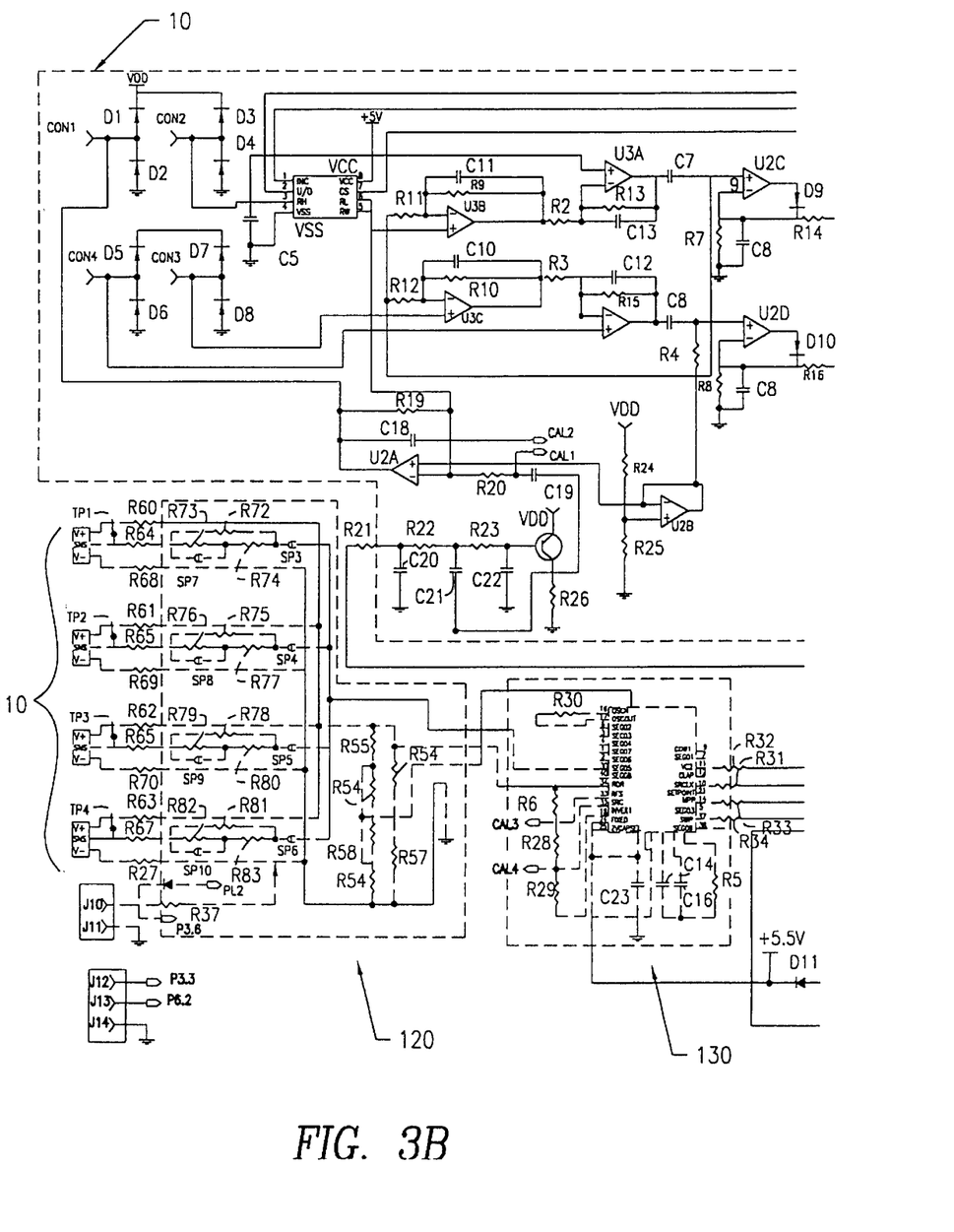
FIG. 3B and FIG. 3C represents a more detailed schematic circuit of the body fat scale according to an embodiment of the present invention.
Figure 3C:
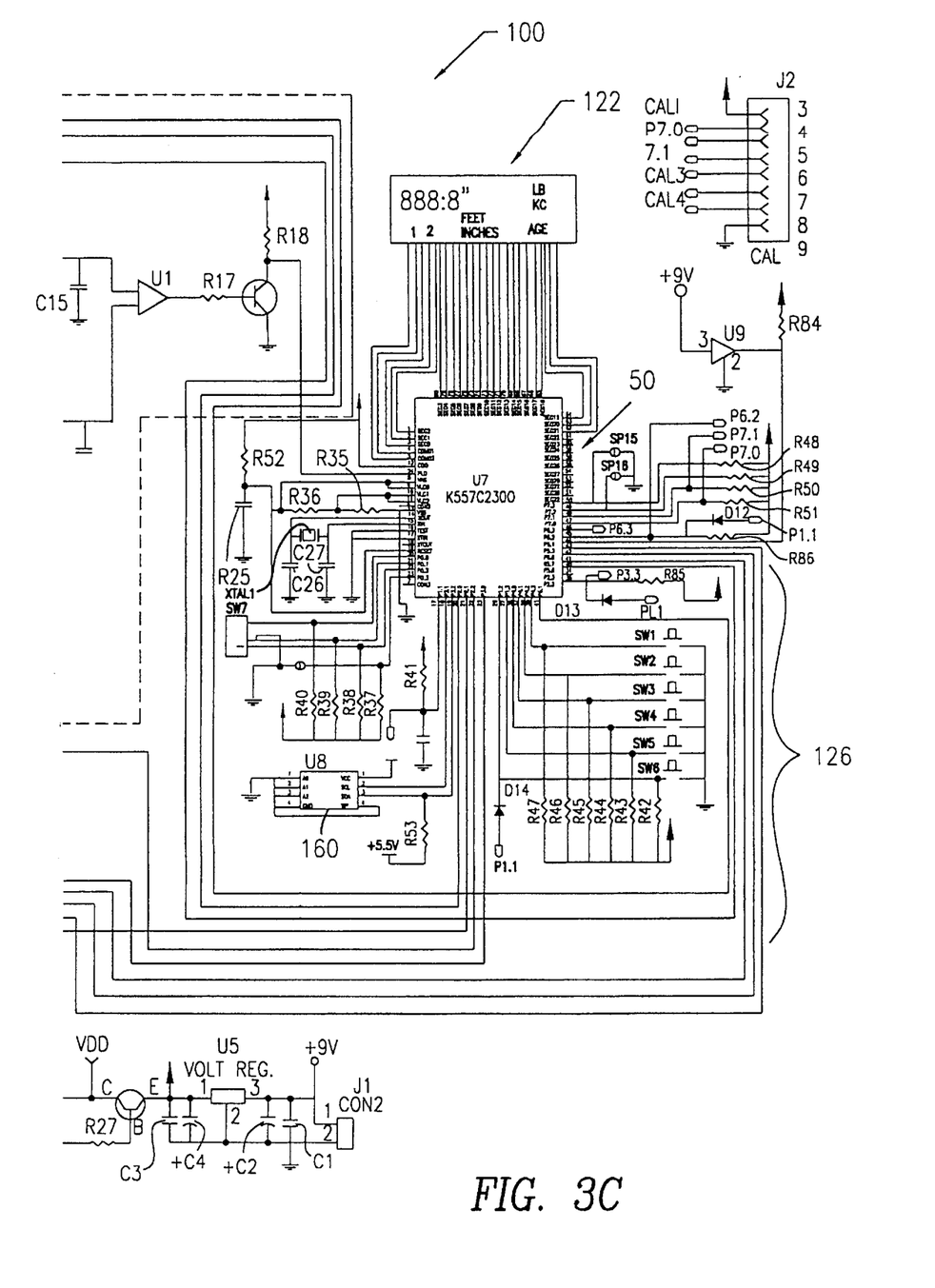

FIG. 3B and FIG. 3C represents a more detailed schematic diagram which includes specific circuit components which perform the actual functions depicted in the high level schematic circuit shown in FIG. 3A. FIG. 3B also illustrates the detailed circuit schematic of the body impedance measurement circuit shown in FIG. 1C. Dashed lines and corresponding reference numerals have been included within the actual circuit implementation of FIG. 3D to better illustrate those parts corresponding to that described within FIG. 3A.

Figure 4:
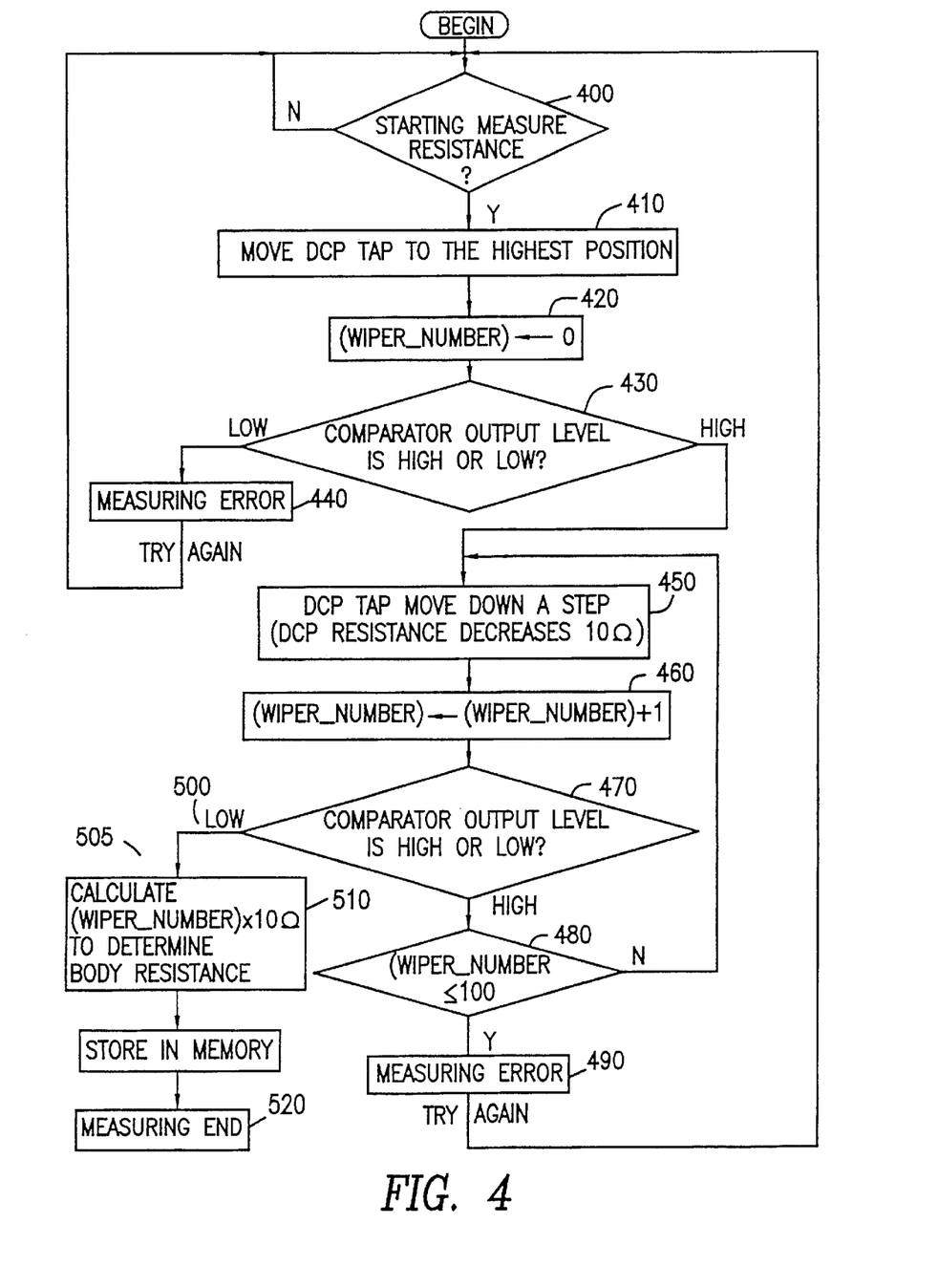
FIG. 4 is a flow chart depicting the method for determining body resistance or impedance according to the present invention.

A diagram of the impedance measurement routine of the microprocessor is depicted in FIG. 4. Referring to FIG. 4, the resistance or impedance measurement process is initiated at block 400. The microprocessor provides a digital control signal to cause the digital potentiometer tap to step to the highest (block 410). A wiper_number variable is incremented (wiper_number=wiper_number+1) and stored in memory within the microprocessor (block 420). The wiper_number is a RAM address within the processor. As shown in block 430, the output signal of the comparator is then compared with a threshold value to determine if the comparator output is at a "high" or "low" state If the output signal of the comparator corresponds to a "high" level, the microprocessor causes the potentiometer tap to step down a predetermined level or increment (block 450), the wiper_number variable is incremented (block 460) and the comparator output is again checked to determine if it is at a "high" or "low" level (block 470). In a preferred embodiment, the step increment is 10, so that the tap resistance decreases by the step value of, for example, 10 ohms. However, any number of increments or step values is contemplated depending on the required accuracy.

If, however, after the first iteration, the microprocessor detects a "low" signal at the comparator output at block 430 (FIG. 4), a measuring error 440 has occurred and the microprocessor returns to block 400 and makes another attempt to measure the body impedance.

The process of stepping the digital potentiometer tap resistance, incrementing the wiper_number, and determining the output level of the comparator, is repeated until the microprocessor detects a state transition of the comparator output from a "high" to "low" state (500). Upon detection of the state transition, the variable wiper_number is retrieved from memory and multiplied by the step increment (in this case 10 ohms) to arrive at the calculated body resistance (block 510). The body resistance is stored in memory and the processing sequence is terminated.

Note that, as shown in decision block 480, the microprocessor also includes error detection and processing circuitry to ensure correct processing of the data. In block 480, the microprocessor compares the value of the variable wiper_number with a predetermined upper limit (for example 100). If the variable value equals (or exceeds) this limit, a measuring error 490 has occurred and the microprocessor resets and restarts the measurement process 400. If, on the other hand, the upper limit has not been reached and the comparator output has not changed state, processing returns to block 450 to continue the stepping of the digital potentiometer resistance.

From the above description, it is apparent that the present technique is a form of substitution principle where the voltage at the sense input is determined using a successive approximation or substitution principle.

The equations are as follows:

$$I\ body = V(50\ \text{kHz})/RS$$

$$V\ sense = n \times V(50\ \text{kHz})\ \text{(based upon comparator detection)}$$

Therefore, the body resistance is given as:

$$R\ Body = V\ sense / I\ Body = n \times R\ set.$$

The microprocessor also includes algorithms which operate to calculate a patient's body fat as identified below from the patient's measured weight using the weight determined from the electronic scale measurement, and the individual's body impedance as determined above. For example, the microprocessor may utilize the determined values of body weight and body impedance or resistance determined via the aforementioned process, in combination with user input data such as height, age and gender, to calculate lean body mass (LBM) according to the equation:

$$LBM = K + A(\text{ht})^2 - B(R) + C(\text{Wt}) - D(\text{age}) + E(\text{Male}),$$

where

Ht=user height (centimeters, cm);
R=determined body impedance (ohms);
Wt=calculated total body weight (kilograms, Kg);
Age=user age;

Male=0 if male, else 1;

and where A, B, C, D, and E are coefficients stored within the microprocessor memory and K is a constant corresponding to the Y-intercept. In a preferred embodiment the coefficients are A=0.00104, B=0.036, C=0.17, D=0, and E=−3.6

Fat mass (FM) may then be calculated to be $$FM = Wt - LBM;$$

and percentage of body fat (% BF) is then obtained as $$\% BF = (FM/Wt)*100.$$

Each of these values may then be displayed to the user via the display unit 122 (see FIG. 2).

Figure 5A:
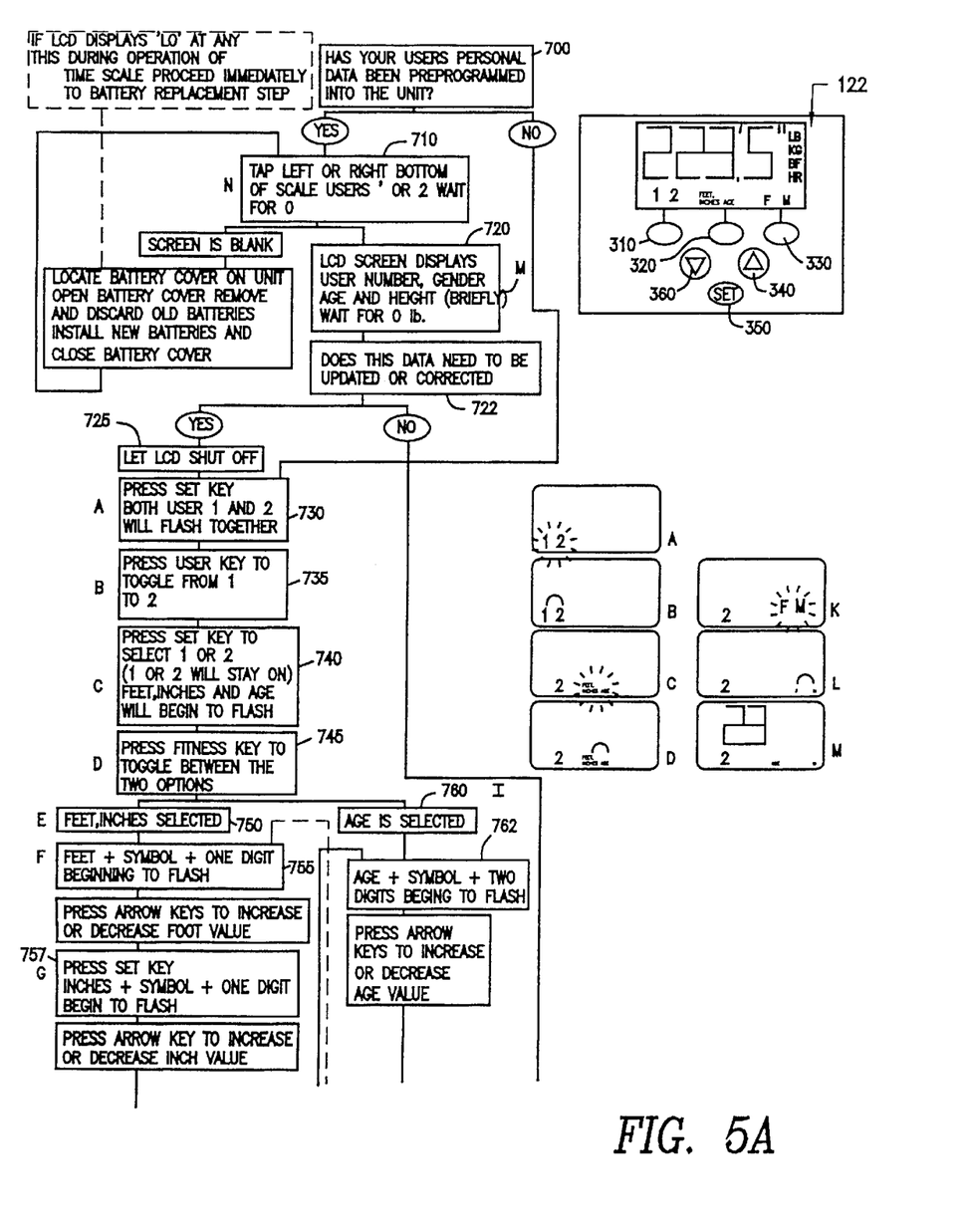
FIG. 5 is a flow chart illustrating the operation of the body fat scale according to an aspect of the present invention.
Figure 5B:
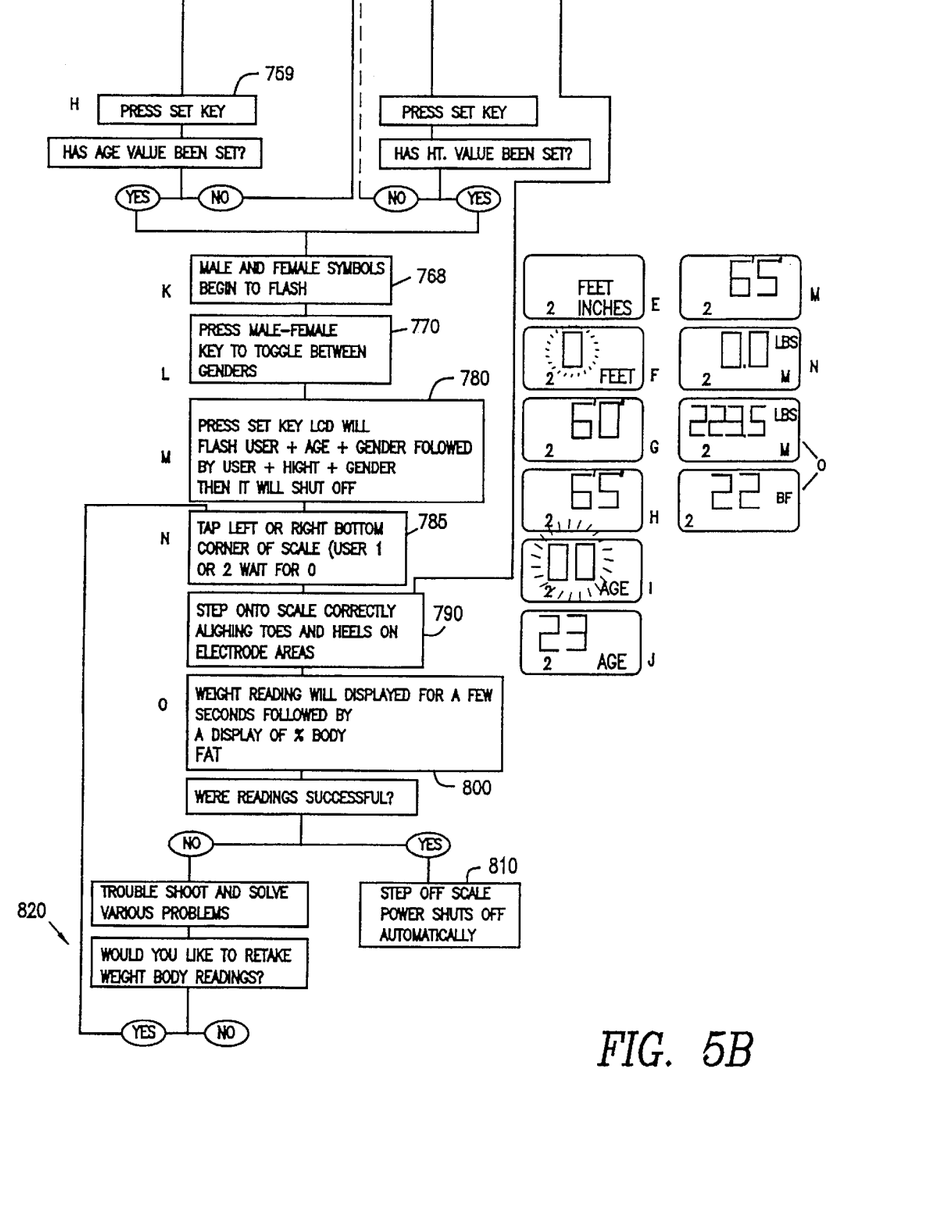

FIG. 5 illustrates an exemplary flow diagram associated with user interaction and display portion of the body composition scale 100 according to a particular embodiment of the invention. Note that character references labeled "A", "B","C" . . . through to "O" associated with blocks 730, 735, 740, 745, 750, 755, 757, 759, 760, 762, 764, 768, 770, 780, 785, and 790, respectively, are used to indicate correspondingly labeled display results to be displayed via LCD display unit 122. Referring to FIG. 5, once a user's personal data has been preprogrammed into the scale (module 700), the user may then press a user selection switch 200 at the bottom of the platform to identify himself as the appropriate user (e.g. user 1 or user 2 on unit 200). Upon initiation (module 710), display screen 122 then displays the user number, gender, age and height of the individual (module 720). If the data needs to be corrected (module 722) or if one's personal data was not preprogrammed into the scale, the user depresses the set key 350 and user key 310 as appropriate to identify the user to the unit and to enter the relevant physiological data, including height (module 750), age (module 760), and gender (module 770). Depressible button 320 on the keypad operates to toggle between height and age parameter data while button 330 provides for gender selection. Up/Down arrow keys 340 and 350 provide the ability to increase or decrease these parametric values. Set key 350 operates to enter the data into memory for later retrieval and or analysis. When all of the user-related physiological data is entered (module 780), display 122 will shut off and the user will provide the appropriate user selection for recalling his or her personal data. The user then steps onto the scale (module 790) and the scale will then calculate the current weight. With the user's feet positioned on the corresponding electrodes as previously described, the body impedance circuit will also be activated to determine the body impedance and software programs will operate on the determined body weight and body impedance to calculate the percent of body fat. The weight reading will then be displayed for a predetermined time period of, for example, a few seconds (module 800) on LCD display 122. Upon expiration of the predetermined time interval, the system will display the calculated % body fat. The user then steps off the scale which causes the system to power down (module 810) If an error occurs during the calculation process (module 820), the user may be given the option as to whether or not another weight reading (or body fat reading) is to be made. Note that, by not depressing activation button 200, the scale according to the present invention operates as simply a body weight scale and does not determine body fat.

It is contemplated that various algorithms may be utilized to arrive at lean body mass, fat mass and body fat composition values based on well known formulas and equations. It is to be understood that one skilled in the art may make many variations and modifications to that described herein. For example, in a preferred embodiment, the potentiometer may be implemented as a half bridge, temperature compensated device for providing a substantially temperature invariant voltage. Alternatively, a device having associated resistance and voltage values selectable by the microcontroller such that the resistance associated with the signal value that causes the comparator output to be nulled represents the body impedance may also be utilized. Numerous other implementations of a potentiometer or such device are contemplated. All such variations and modifications of the above components and structures are intended to be included within the scope of the invention as defined in the appended claims.

What is claimed is:

1. A method of determining body impedance comprising the steps of:
 coupling a first pair of electrodes to one portion of the body and applying a current through said electrodes;
 coupling a second pair of electrodes to another portion of the body;
 sensing a first voltage signal indicative of the voltage across said second pair of electrodes due to said current applied to said first pair of electrodes;
 providing an impedance in electrical communication with said first pair of electrodes so as to produce a second voltage signal; and
 comparing said first and second voltage signals to produce a control signal and adjusting said impedance in response to said control signal until said first and second signals are substantially equal, wherein the adjusted impedance corresponds to said body impedance.

2. The method according to claim 1, wherein the step of coupling said first pair of electrodes to one portion of the body comprises connecting one electrode to a toe portion of a patient's left foot and the other of said first pair of electrodes to the toe portion of a patient's right foot.

3. The method according to claim 1, wherein the step of coupling said first pair of electrodes to one portion of the body comprises connecting one electrode to a heel portion of a patient's left foot and the other of said first pair of electrodes to the heel portion of a patient's right foot.

4. The method according to claim 1, wherein the step of adjusting said impedance comprises changing the impedance value in a stepped fashion and iteratively comparing said first and second voltage signals until said voltage signals are substantially equal.

5. A circuit for measuring body impedance comprising:
 a voltage source having a predetermined frequency;
 a first pair of electrodes adapted to receive one portion of the body for applying a current to said body through said electrodes;
 a second pair of electrodes adapted to receive another portion of the body for sensing a voltage therebetween in accordance with the current through said first electrodes;
 a comparator having first and second inputs and an output for producing an output signal based on signals applied to said first and second inputs;
 first means coupled to one of said comparator inputs and responsive to the voltage across the second pair of electrodes for providing an input signal to said first comparator input;
 an adjustable impedance device coupled to the second input of said comparator for developing a first voltage signal applied to said second comparator input; and
 means responsive to the output signal of the comparator for varying the impedance of said impedance device to cause a corresponding change in said first voltage, wherein when said voltage at said first input corresponds to the voltage at said second input of said comparator, said comparator output signal transitions from a first state to a second state indicative of a null condition, wherein the body impedance value corresponds to said impedance value of said impedance device.

6. The circuit according to claim 5, wherein said first means includes:
 a differential amplifier arrangement having an input coupled to said second pair of electrodes and an output for providing said input signal.

7. The circuit according to claim 5, wherein said adjusting means comprises a microcontroller.

8. The circuit according to claim 5, wherein said variable impedance device comprises a digital potentiometer.

9. The circuit according to claim 5, wherein said variable impedance device is responsive to said voltage source.

10. The circuit according to claim 5, wherein said voltage source is sinusoidal.

11. The circuit according to claim 10, wherein said sinusoidal voltage source has a frequency of approximately 50 kHz.

12. The circuit according to claim 5, wherein said first pair of electrodes are formed of a conductive resin.

13. The circuit according to claim 5, wherein said second pair of electrodes are formed of a conductive resin.

14. The circuit according to claim 5, wherein said one body portion comprises a patient's toes.

15. The circuit according to claim 5, wherein said another portion comprises a patient's heels.

16. A circuit for determining impedance of a body comprising:
 a first pair of electrodes coupled to a first body portion for providing a constant current thereto;
 a second pair of electrodes coupled to a second body portion for sensing a voltage signal therebetween;
 variable resistor means for generating a first voltage signal;
 a comparator having inputs for receiving first and second input signals and an output terminal for providing an output signal;
 means responsive to said output signal for controlling said first voltage signal to produce a null output signal, wherein the value of said body impedance corresponds to the resistive value associated with said resistor means when said output signal is nulled.

17. The circuit of claim 16, wherein said first and second pairs of electrodes are mounted on a platform scale and positioned to receive the toe and heel portions, respectively, of a patient's feet.

18. The circuit of claim 16, wherein said electrodes are formed of a conductive paint.

19. The circuit of claim 16, wherein said metal coating is disposed on a plastic.

20. An apparatus for measuring body composition in a patient's body comprising:
 a measuring station for measuring impedance between the patient's feet and an operating circuit coupled to said measuring station, said measuring station including:

a base on which a patient can stand, first and second pairs of electrodes mounted on said base, said first pair of electrodes adapted to receive one portion of the body for transmitting a drive current thereto;

the second pair of electrodes adapted to receive another portion of the body for sensing a voltage therebetween;

a comparator having inputs for receiving first and second input signals and an output terminal for providing an output signal;

first means responsive to the voltage across the second pair of electrodes for providing one input signal to the comparator, second means coupled to the second input of the comparator for providing a second input signal thereto; and means responsive to the output signal of the comparator for producing a control signal to said second means for adjusting the voltage of said second input signal; wherein when said voltage of said second means corresponds to said voltage output produced by said first means, said comparator output signal is indicative of a null condition, wherein the body impedance value corresponds to the ratio of the voltage at said second means to said drive current; and means for determining body composition as a function of said body impedance value.

21. In a circuit for determining impedance of a body comprising a first pair of electrodes coupled to a first body portion for providing a current thereto; a second pair of electrodes coupled to a second body portion for sensing a voltage signal therebetween; the improvement therewith comprising:

servo means for producing an output signal indicative of a difference in voltage between the second pair of electrodes and a variable signal from a generator, said variable signal varying in response to said output signal such that when said output signal corresponds to a null output, the value of said variable signal is indicative of said body impedance.

22. An apparatus for determining impedance of a body comprising:

first and second electrodes defining a first pair positioned on a platform and spaced apart for engaging respective first and second body parts;

third and fourth electrodes defining a second pair positioned on a platform and spaced apart for engaging respective third and fourth body parts;

means for providing a current to said first and second electrodes to cause a voltage to be produced at said third and fourth electrodes;

a servo system coupled between said first and second pairs electrodes for producing an output signal indicative of a difference in voltage between the second pair of electrodes and a variable signal from a generator, said variable signal varying in response to said output signal such that when said output signal corresponds to a null output, the value of said variable signal is indicative of said body impedance.

23. The circuit according to claim 21, wherein said generator comprises a digital potentiometer.

24. The apparatus according to claim 22, wherein said servo system includes a comparator for producing said output signal, and a microcontroller responsive to said output signal for producing a signal to said generator to cause adjustment of said variable signal.

25. A method of determining body impedance comprising the steps of:

coupling a first pair of electrodes to one portion of the body and applying a current through said electrodes;

coupling a second pair of electrodes to another portion of the body;

sensing a first voltage signal indicative of the voltage across said second pair of electrodes due to said current applied to said first pair of electrodes;

providing an impedance in electrical communication with said first pair of electrodes so as to produce a second voltage signal;

comparing said first and second voltage signals and generating a control signal associated with a first state in response to said comparison;

adjusting said impedance in response to said control signal; and repeating said steps of comparing said first and second voltage signals and adjusting said impedance until said control signal transitions from said first state to a second state based on said comparison, wherein the adjusted impedance corresponds to said body impedance.

* * * * *

UNITED STATES PATENT AND TRADEMARK OFFICE
CERTIFICATE OF CORRECTION

PATENT NO.    : 6,292,690 B1
DATED         : September 18, 2001
INVENTOR(S)   : Steven P. Petrucelli and Stephen A. Orbine

It is certified that error appears in the above-identified patent and that said Letters Patent is hereby corrected as shown below:

<u>Title page,</u>
Item [73] should read:

-- [73]   Assignee: Measurement Specialties, Inc., Fairfield, NJ (US) --

Signed and Sealed this

First Day of April, 2003

JAMES E. ROGAN
*Director of the United States Patent and Trademark Office*